United States Patent
Beckhaus et al.

(10) Patent No.: US 7,322,746 B2
(45) Date of Patent: Jan. 29, 2008

(54) X-RAY SENSITIVE CAMERA COMPRISING TWO IMAGE RECEIVERS AND X-RAY DEVICE

(75) Inventors: Christian Beckhaus, Darmstadt (DE);
Uwe Zeller, Biberach/Riss (DE);
Martin Eckert, Hemsbach (DE);
Ulrich Schulze-Ganzlin, Lorsch (DE);
Werner Günther, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 10/550,304

(22) PCT Filed: Mar. 24, 2004

(86) PCT No.: PCT/DE2004/000619

§ 371 (c)(1),
(2), (4) Date: Sep. 22, 2005

(87) PCT Pub. No.: WO2004/084729

PCT Pub. Date: Oct. 7, 2004

(65) Prior Publication Data

US 2006/0227934 A1    Oct. 12, 2006

(30) Foreign Application Priority Data

Mar. 24, 2003 (DE) .................. 103 13 109

(51) Int. Cl.
*G21N 23/083* (2006.01)
*H05G 1/00* (2006.01)

(52) U.S. Cl. ........................ 378/205; 378/19

(58) Field of Classification Search .......... 378/19, 378/21, 22, 98.8, 38–40, 146, 205; 250/370.09
See application file for complete search history.

(56) References Cited

U.S. PATENT DOCUMENTS

| | | | |
|---|---|---|---|
| 4,847,881 A | 7/1989 | Heubeck | |
| 4,878,234 A | 10/1989 | Pfeiffer et al. | |
| 5,058,147 A * | 10/1991 | Nishikawa et al. | 378/38 |
| 5,511,106 A | 4/1996 | Doebert et al. | |
| 5,579,366 A | 11/1996 | Doebert et al. | |
| 5,784,429 A | 7/1998 | Arai | |
| 5,995,583 A | 11/1999 | Schick et al. | |
| 6,049,584 A * | 4/2000 | Pfeiffer | 378/39 |
| 6,055,292 A * | 4/2000 | Zeller et al. | 378/21 |
| 7,092,483 B2 * | 8/2006 | Nyholm | 378/38 |
| 2002/0085673 A1 | 7/2002 | Rinaldi et al. | |

* cited by examiner

*Primary Examiner*—Edward J. Glick
*Assistant Examiner*—Anastasia S. Midkiff
(74) *Attorney, Agent, or Firm*—Dykema Gossett PLLC

(57) ABSTRACT

The invention relates to an X-ray sensitive camera (1, 55) comprising a first X-ray sensitive image receiver (4), for creating a first tomogram with a first depth of field profile, in addition to a second X-ray sensitive image receiver (5) for creating a second tomogram with a second depth of field profile. The invention also relates to an X-ray device comprising an image receiver (4, 5) that is contained in an X-ray sensitive camera (55), in addition to an X-ray emitter (52) with a primary diaphragm (57) and adjusting means (43, 44) for the image receiver and/or X-ray emitter and/or primary diaphragm and/or a combination thereof. The camera is equipped with a second image receiver (5), which can be brought into the beam path (54) of the X-ray emitter using the adjusting means (43, 44).

3 Claims, 7 Drawing Sheets

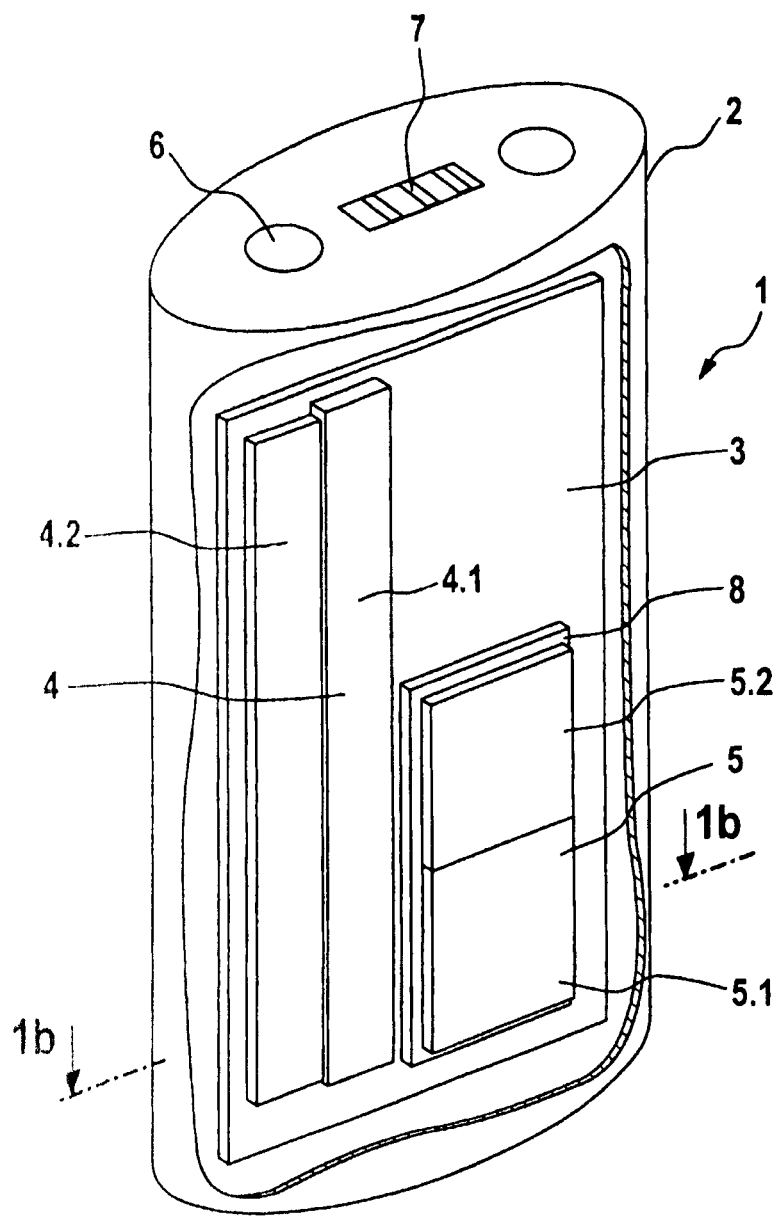
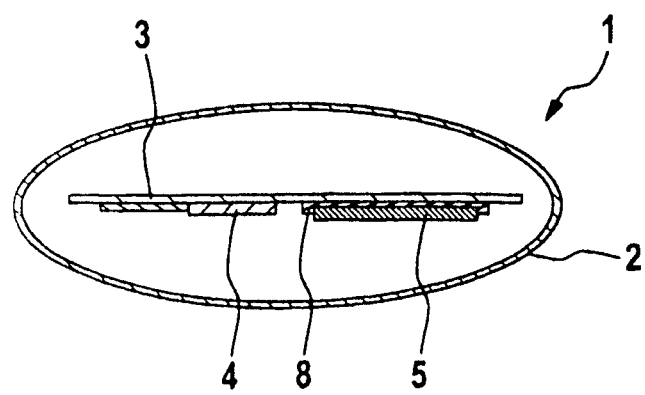

X-RAY SENSITIVE CAMERA COMPRISING TWO IMAGE RECEIVERS AND X-RAY DEVICE

The invention relates to an X-ray sensitive camera comprising an X-ray sensitive image detector for creating a first tomographic image with a first depth of focus profile and to an X-ray system comprising such a camera.

Such a camera is used for the creation of dental panoramic tomographic images by means of X-ray apparatus.

The depth of focus is determined by the resolution just acceptable in the X-ray image to be created, there being a smooth transition from "in focus" (maximum resolution) to "out of focus". This phenomenon of smudging is well known and is based substantially on the speed of the X-ray fan beam on the one hand and the speed of the film or its digital counterpart on the other hand.

DESCRIPTION OF THE RELATED ART

A dental X-ray diagnostic device for producing panoramic tomographic images of a patient's jaw is disclosed in EP 0 229 971. In addition to panoramic tomographic images (PAN images), images of one or more user-defined, selectable jaw sections can be produced in a plurality of superposed layers (multilayer images). Furthermore, a film cassette holder is mounted on a rotatable unit bearing the X-ray emitter so that it can be pivoted from an operating position to a non-operating position, which makes it possible to produce teleradiographic images (ceph images), as the X-ray emitter can then direct a beam unhindered past the film cassette holder.

An X-ray diagnostic device for the production of X-ray images of parts of a patient's body is disclosed in EP 0 632 994 A1, in which there is a line detector camera with an X-ray detector, the width of which corresponds to the width or the length of the body part to be imaged. The line detector camera can be moved together with the X-ray source along the part of the body to be imaged via regulating means. The X-ray diagnostic device can thus be configured to produce a PAN image as well as a teleradiographic image (ceph image), and the line detector camera for producing the required image can be unplugged and replugged, for which purpose it is equipped with a connector containing connecting means for a detachable mechanical and electrical connection with a holder. Furthermore, various possibilities are disclosed for aiming the X-ray fan beam when producing the teleradiographic image using a movable emitter or a primary diaphragm or a combination of the two.

A camera that is capable of being unplugged and replugged is described in detail in EP 0 634 671 A1, particular attention being paid to the detachable mounting of the camera on a holder.

A detector system for the production of X-ray images is disclosed in EP 0 858 773 A2 and consists of detectors having dimensions similar to those of the detector of an intraoral sensor. The detector system is so constructed that transversal slice acquisition images (TSA images) may be produced and the detector system mounted for displacement along its longitudinal axis inside the line detector camera. The detector elements can be displaced along the main axis of the detector by adjustment means.

The sensors used in EP 0 858 773 A2 to produce a PAN or a ceph image typically have an image height of from 135 to 180 mm and an image width of approx. 6 mm. The sensors used to produce TSA images typically have dimensions of about 30×20 mm. The difference in width results from the fact that, in the case of a PAN image, it is desirable for the layer thickness (depth of focus) of the sharp slice to be at least the same as the thickness of the object being imaged, whereas, by contrast, the layer thickness (depth of focus) of the sharp image in the case of a TSA image is about 1 to 3 mm.

However, the reduced layer thickness and the reduced depth of focus must necessarily require an increase in the width of the image detector used for the creation of images with a CCD sensor operating in TDI mode. The same applies to image detectors that produce individual plane images that are subsequently computed to a tomographic image showing the required depth of focus. CMOS detectors exemplify image detectors of this type.

Although prior art technology already provides for the camera used for the creation of a panoramic image to be unplugged and then replugged for the production of a ceph image, for the purpose of producing a TSA image an additional X-ray system is still required which provides the sensor dimensions necessary for this purpose.

SUMMARY AND OBJECTS OF THE INVENTION

According to the invention, an X-ray-sensitive camera is proposed which has a first X-ray-sensitive image detector for creating a first tomographic image having a first depth of focus profile. Furthermore, a second X-ray-sensitive image detector for the creation of a second tomographic image with a second depth of focus profile is provided.

This camera is thus suitable for the creation of different types of tomographic images.

According to a first development, the second depth of focus profile is smaller than the first depth of focus profile. Such a camera is therefore suitable not only for the creation of panoramic tomographic images but also for the creation of lateral or transverse tomographic images, usually designated as multilayer images. The invention thus makes it possible to create PAN or TSA images with one and the same camera.

According to another development, the image-detecting active surface of the second image detector can be at least twice as large as the first image detector, in a first dimension. Furthermore, the second image detector may be not more than half as large as the first image detector, in a second dimension. The advantage of this is that, on the one hand, existing elongated line sensors having dimensions suitable for PAN or ceph images and, on the other hand, existing face sensors having the required width for intraoral images can be used as image detectors. It is not necessary to provide a PAN sensor having a width sufficient for the production of TSA images, which would cost considerably more than the two individual sensors together.

According to another development, the image detectors are installed in a common casing with the camera.

The second image detector is advantageously mounted alongside the first image detector. The shoulder freedom of the patient to be X-rayed is thus not impaired by the camera.

The second image detector is advantageously mounted on the rear side of the first image detector. Such a camera can be built into traditional X-ray systems for the production of PAN images and thus provides the option of retrofitting for the production of multilayer images, especially if it is possible, for example, to unplug the camera, turn it around relatively to the X-ray emitter, and replug it.

The camera is advantageously designed so that the second image detector can be retrofitted. In this case it is possible to first equip the X-ray system with a camera for the production of PAN images and then, when necessary, install the second image detector in the camera for the production of multilayer images.

According to another development, the second image detector is part of the first image detector or vice versa. On the one hand, this allows the image-detecting surface provided by the second image detector to be used even if no images typical for this type of detector are being produced, and, on the other hand, it allows part of the first image detector to be used for the production of the image using the second image detector.

According to another development, adjustment means are provided to bring either the first or the second image detector, as desired, into proper alignment with an X-ray emitter for the production of the respective X-ray image.

The adjustment means and both image detectors can be built into a common casing with the camera or on the camera casing and in the region of connecting means for mounting the camera on a support, and the camera in its entirety is then adjustable relatively to said connecting means. In the latter case it is also easy to regulate positioning of the camera visually from outside and confirm that the correct sensor has been moved into the proper position for creation of the image. Furthermore, the camera casing can be kept more compact than when the sensor adjustment means are disposed only within the camera casing.

If the camera has a radiolucent region, it is possible to leave the camera in the X-ray fan beam for the creation of an additional image without any significant negative impact on the image production. The camera can therefore remain in place and need not be removed.

According to one development, the radiolucent region is located between the first and second image detectors.

According to another development, the radiolucent region is located alongside the first and second image detectors.

The invention also relates to an X-ray system having an image detector built into an X-ray-sensitive camera, which system also comprises an X-ray emitter having a primary diaphragm and adjustment means for the image detector and/or the X-ray emitter and/or the primary diaphragm and/or combinations thereof. Within the camera there is provided a second image detector, and the second image detector is capable of being moved into the optical path of the X-ray emitter by means of the adjustment means.

Using such an X-ray system, it is possible, without changing the camera, to create, say, both panoramic tomographic images and multilayer images, provided the second image detector is appropriately constructed. Advantageously, the camera and the X-ray emitter used for this purpose are mounted on a common support, as is well known in X-ray systems adapted for the creation of panoramic tomographic images.

Advantageously, adjustment means are provided which cooperate with the camera, which adjustment means can be built into the camera casing or built into connecting means between the camera and the support or mounted on the support itself.

Adjustment means disposed inside the casing are shielded from outside influences. There is relatively more space available when the adjustment means are mounted on the support, and the camera can be made smaller and lighter.

The adjustment range of the camera is equal to at least one width of the first sensor so that the latter can be moved completely away from the optical path of the X-ray fan beam when an image is to be created using the second image detector.

The X-ray system can, in a development, be additionally equipped with a device for the production of teleradiographic images using an additional image detector. When the X-ray emitter is aligned to produce such a ceph image, the camera is disposed in the region of the path of radiation between the X-ray emitter and the image detector of the device for the production of the ceph image, and in this region the camera is radiolucent.

Alternatively, the path of adjustment can be dimensioned such that when the X-ray emitter is aligned for the purpose of creating teleradiographic images, the camera can be moved outside the path of radiation between the X-ray emitter and the image detector of the device for the creation of teleradiographic images.

Both methods have the advantage of not requiring manual intervention for switching the imaging method from close-up tomographic images (PAN/TSA) to teleradio-graphic images (ceph images).

BRIEF DESCRIPTION OF THE DRAWINGS

An exemplary embodiment of the invention is illustrated in the drawings, in which:

FIGS. 1a and 1b show a camera with two different image detectors located adjacent to each other.

DETAILED DESCRIPTION OF EXEMPLARY EMBODIMENTS OF THE INVENTION

Figure 2A:
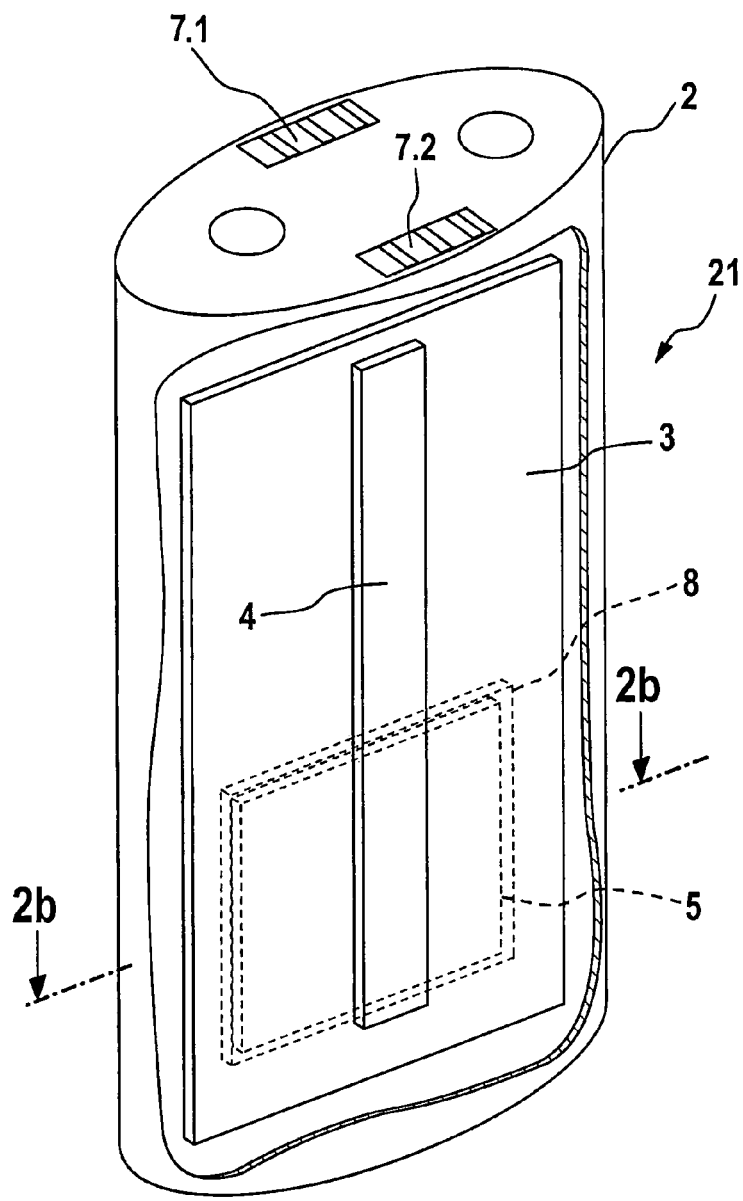
FIGS. 2a and 2b show a camera with two different sensors that are oriented back to back.

A camera 1 of the invention is illustrated in FIG. 1a in a perspective view. Camera 1 has a casing 2 in which a circuit board 3 is installed. A first image detector 4 in the form of a line sensor is provided on board 3, which detector is a CCD sensor in this exemplary embodiment and has a length which is many times greater than its width.

The image detector 4 can be divided into an image detecting area in the form of a CCD sensor 4.1 and read-out electronics 4.2. Such forms of an image detector are well known in the prior art. In principle, image detectors such as CMOS sensors that produce individual images in the form of a plane image can also be used.

Adjacent to the first image detector 4 there is provided an additional image detector 5, which is again divided into an image-detecting zone 5.1 in the form of a CCD sensor and a read-out zone 5.2 and which is likewise mounted on support 3.

Casing 2 is equipped with mechanical and electrical connecting means 6, 7 so that camera 1 can be mounted on a standard support structure (not shown).

A cross section through the camera 1 taken along the line 1b-1b in FIG. 1a is illustrated in FIG. 1b. Board 3 with the first image detector 4 and the second image detector 5 is shown in casing 2, and the second image detector 5 is installed in a holding device 8 on board 3.

FIG. 2a shows a camera 21, which likewise has a casing 2 and a board 3, and the first image detector 4 is mounted on board 3. The second image detector 5, represented by dashed lines, is mounted on the rear side of board 3.

In order to ensure electrical contact when the camera 21 is rotated, the electrical contact 7 is duplicated as 7.1 and 7.2. This double contact can obviously also be provided on means (not shown) for coupling the camera to an X-ray system.

Figure 6:
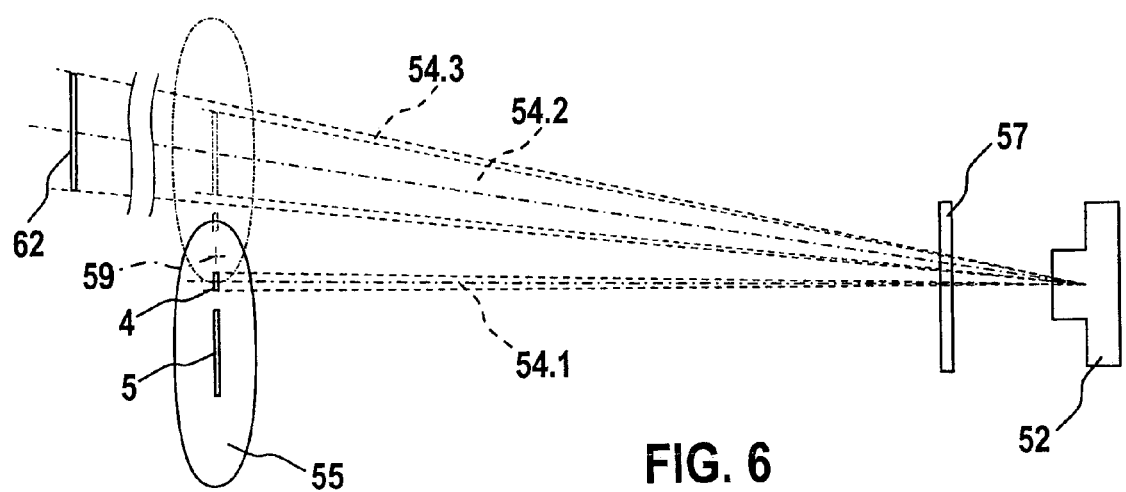
FIG. 6 is a further diagram illustrating an eccentrically pivoted camera.

When the camera is rotated as in FIG. 6, a connection that can be unplugged is not required. This rotation can be achieved by a motor or manually.

Figure 2B:
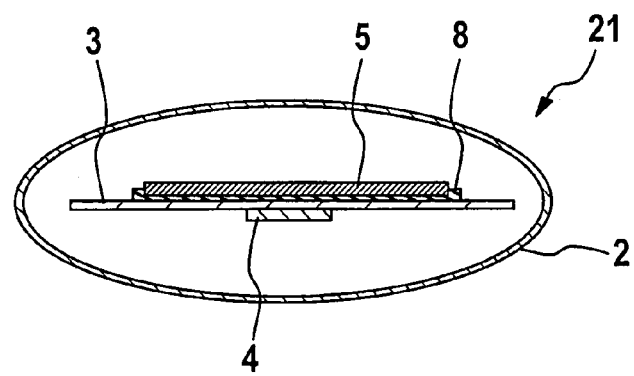
Figure 3D:
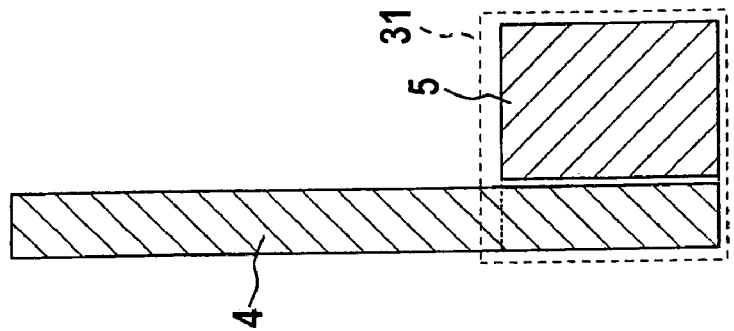
FIGS. 3a to 3d show various configurations of two image detectors, which together form a single detector.
Figure 3C:
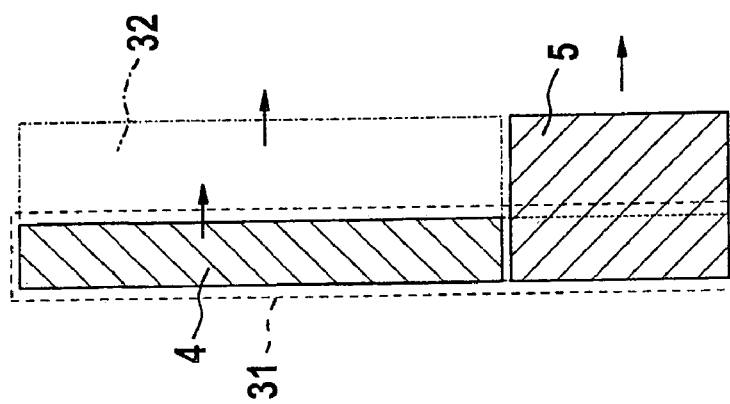
Figure 3B:
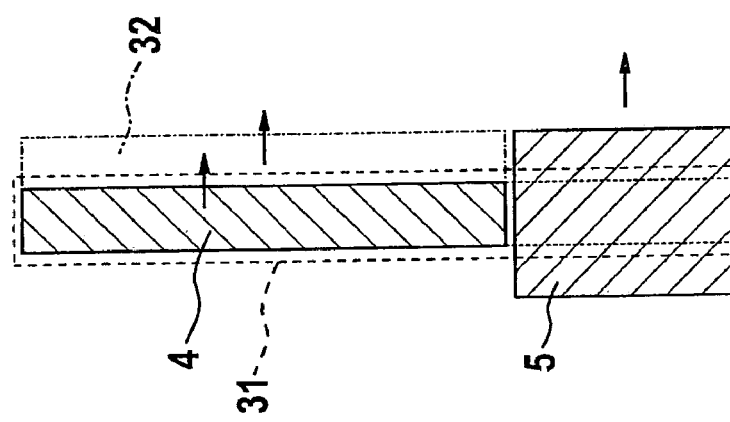
Figure 3A:
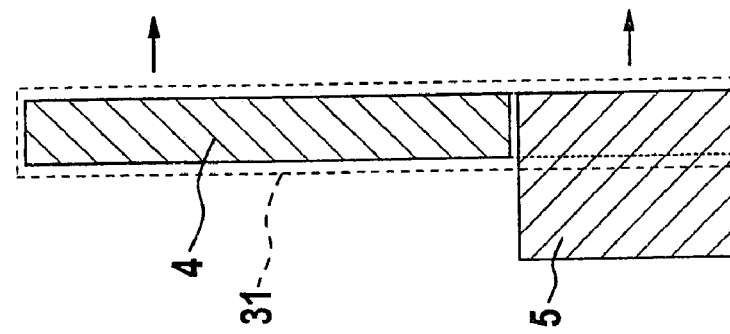

The cross-sectional illustration of FIG. 2b clearly shows the back-to-back arrangement of the two image detectors 4, 5, that is, on either side of support 3. Image detector 5 is installed in the holding device 8.

FIGS. 3a to 3d show different embodiments of an image detector forming a "virtual" combination of the two image detectors 4, 5 present. The virtual image detector 31 can be designed such that the length of the line detector of image detector 4 is increased by the required amount (see FIGS. 3a to 3c). The virtual image detector 31 can alternatively be designed such that the image detector 4 in the form of a line detector increases the width of image detector 5 in the form of a face sensor (see FIG. 3d).

In all cases care must be taken to ensure that the direction of motion of the charges on image detector 4 carrying the image signals in TDI mode is made to comply with the direction of motion of the charges on image detector 5, as indicated by the arrows.

Of course, it must be ensured that appropriate corrective measures are effected in the transition region between the two image detectors 4, 5, in order to compensate for image distortions. Such corrections can be fixed or variable by appropriate circuitry or they can be subsequently effected using appropriate correction methods.

Since an X-ray system for the production of a PAN image will be considered to be the basic device on account of the fact that such images are produced more frequently, the camera can be designed so that the image detector 5 for the TSA image can be retrofitted. Retrofitting can be carried out, for example, by opening the casing and plugging in the image detector 5 in an appropriate place and making any additional necessary electrical or mechanical connections.

Prior art X-ray systems for the production of PAN images have fixed connecting means between the X-ray emitter on the one hand and the detector on the other hand so that both are moved together as a unit. As a rule, the detector as such is fastened rigidly to the common support together with the X-ray emitter.

Figure 4A:
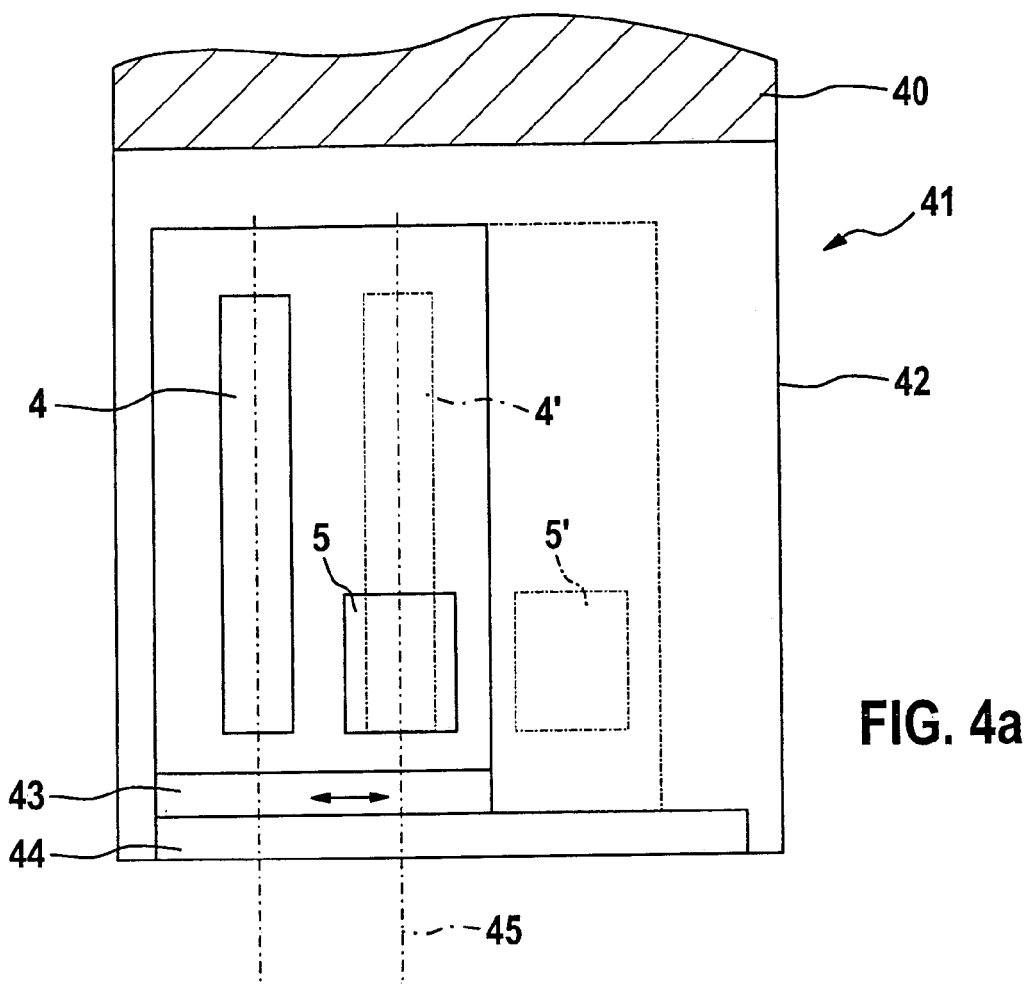
FIGS. 4a and 4b show a first and second adjustment mechanism for the displacement of the sensors within a camera casing or for the displacement of the camera housing.
Figure 4B:
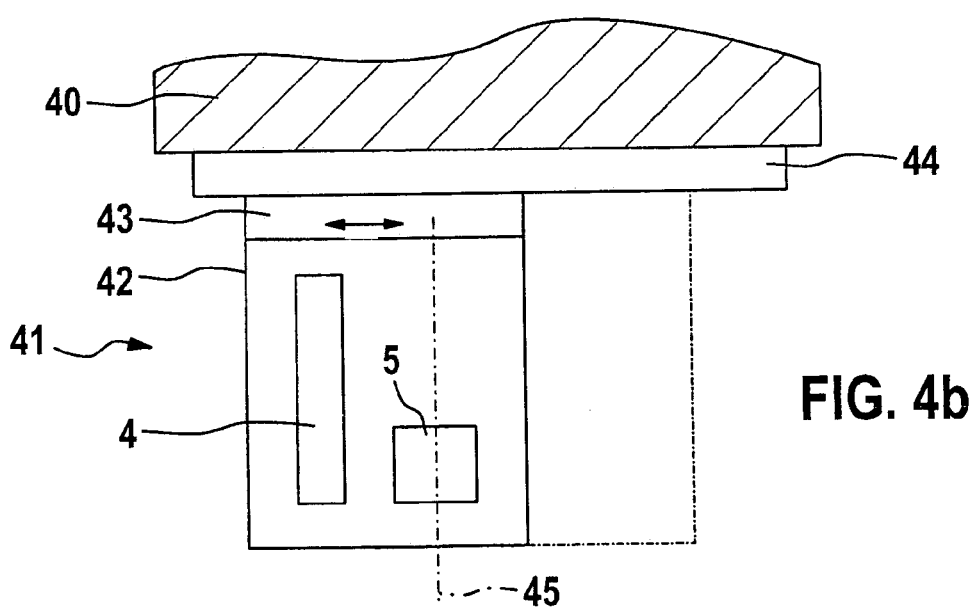

A first and second adjustment mechanism for positioning the image detectors are illustrated in FIGS. 4a and 4b. The camera 41, which is attached to a support structure 40, has a casing 42, in which the image detectors 4, 5 are guided by an adjustment mechanism in the form of a carriage 43 on a guide track 44. The image detectors 4, 5 can thus be moved with the carriage 43 and the adjustment mechanism 44 from the position illustrated to the dashed line position 4', 5', so that instead of the face sensor of the image detector 5, the line detector of image detector 4 moves into the X-ray fan beam represented by the line 45.

In FIG. 4b, the adjustment mechanism is located between a camera 41 and the support 40. Camera 41 is mounted via its casing 42 on the support structure 40 for displacement thereon, as represented by carriage 43 attached to the camera and guide track 44 attached to the support 40. This allows the entire camera 41 to be moved from the position illustrated to the position represented by the dashed line, so that the X-ray beam, again illustrated by line 45, is aligned not with image detector 5 but with image detector 4.

Camera 41 is attached by connecting means and these connecting means can also include adjustment means. This, however, is not illustrated.

Alternatively, a TSA image can be produced with a motor-driven camera holder, in which the sensor is positioned according to the desired mode of operation. The motor-driven camera holder forms the connection between the connecting means of the camera and the support. Said holder can be designed so that the camera plus connecting means can be moved along a guide track or pivoted by means of a pivoting mechanism. Thus the camera can be moved automatically into the optimal position in the system. A direct image series for a PAN image followed by a multilayer image can be produced in this manner without any additional intervention on the part of the operator.

Figure 5A:
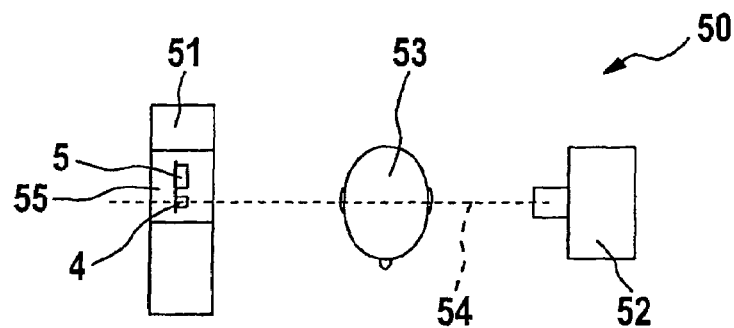
FIG. 5a shows a diagram of an X-ray system of the invention for the production of PAN and TSA images in a first imaging situation (PAN)

Main parts of an X-ray system 50 are illustrated in FIG. 5a, specifically an imaging device with an imaging unit 51 and an X-ray emitter 52, in which the object to be examined in the form of a patient's head 53 is positioned between the X-ray emitter 52 and the imaging unit 51. For the production of a panoramic tomographic image, the X-ray beam 54 emitted from the X-ray emitter 52 is directed to the image detector 4 constructed in the form of a line detector, so that the required length for producing a PAN image of the upper and lower jawbones is provided. The detecting unit 51 and X-ray emitter 52 are mounted on a common support and are adapted for movement around at least part of the object to be examined.

Meanwhile, the image detector 5 in the form of a face sensor is in a neutral position outside the X-ray beam 54.

Figure 5B:
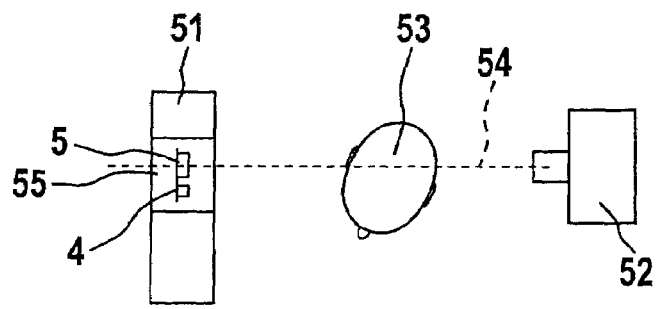
FIG. 5b shows the X-ray system of FIG. 5a in a second imaging position (TSA)

An imaging situation for producing a multilayer image of a specific subregion of the jawbone, such as a single tooth, is illustrated in FIG. 5b. The camera disposed on the imaging unit 51 is now aligned so that the image detector 5 is exposed to the X-ray beam 54, and the image detector 4 is now in a neutral position.

Accordingly, in the case of a camera having a sensor configuration as in FIGS. 2a and 2b, either the image detector 4 or the image detector 5 will be oriented toward the X-ray emitter. For this purpose, the camera can either be unplugged and replugged or automatically rotated by a motorized adjustment mechanism.

Obvious to the person skilled in the art, but not always illustrated in the figures, is the use of a primary diaphragm with mechanically rigid default orifices or an orifice that can be regulated by moveable beam-delimiting elements (not shown) for restricting the extent of the X-ray beam, the extent of the X-ray beam being such that it substantially matches the image-sensitive area of the image detector 4 or 5 or even perfectly fits the image-sensitive surfaces of the image detectors 4 and 5 respectively, in accordance with the relevant standards. Radiation bombardment by X-rays not needed for the production of the image is thus avoided.

Figure 5C:
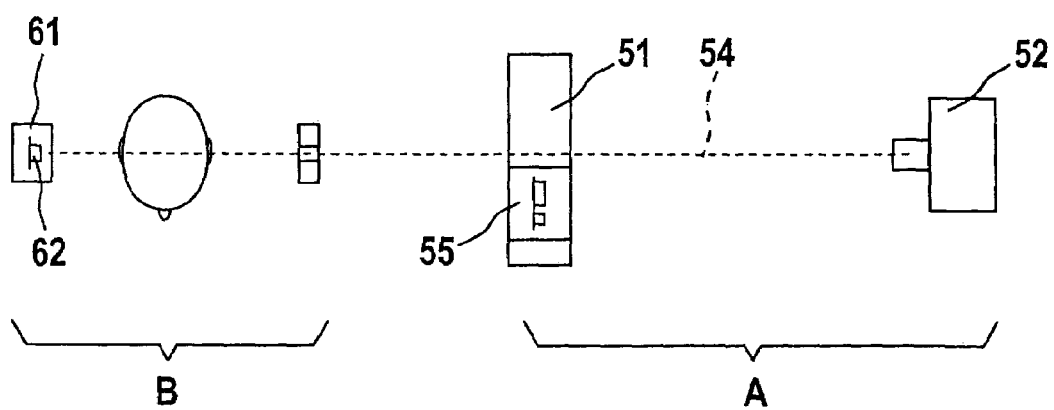
FIG. 5c shows an additional X-ray system having a third imaging position (ceph)

A diagram illustrating the production of a ceph image is shown in FIG. 5c.

A ceph image can be produced in an X-ray system equipped with a PAN unit "A" and a ceph unit "B" by bringing a separate camera 61, equipped with an image detector 62 with a line sensor of appropriate length for the production of the ceph image, into the ceph position. The camera 55 for the production of the PAN image and the multilayer image is positioned so that the X-ray beam 54 emitted from the emitter 52 is directed past the casing of said camera 55.

If a separate ceph sensor is not provided, the first camera 55 can be unplugged and replugged manually if the image detector for the production of the PAN image located therein is also long enough to fit the dimensions required to produce the ceph image.

Figure 5D:
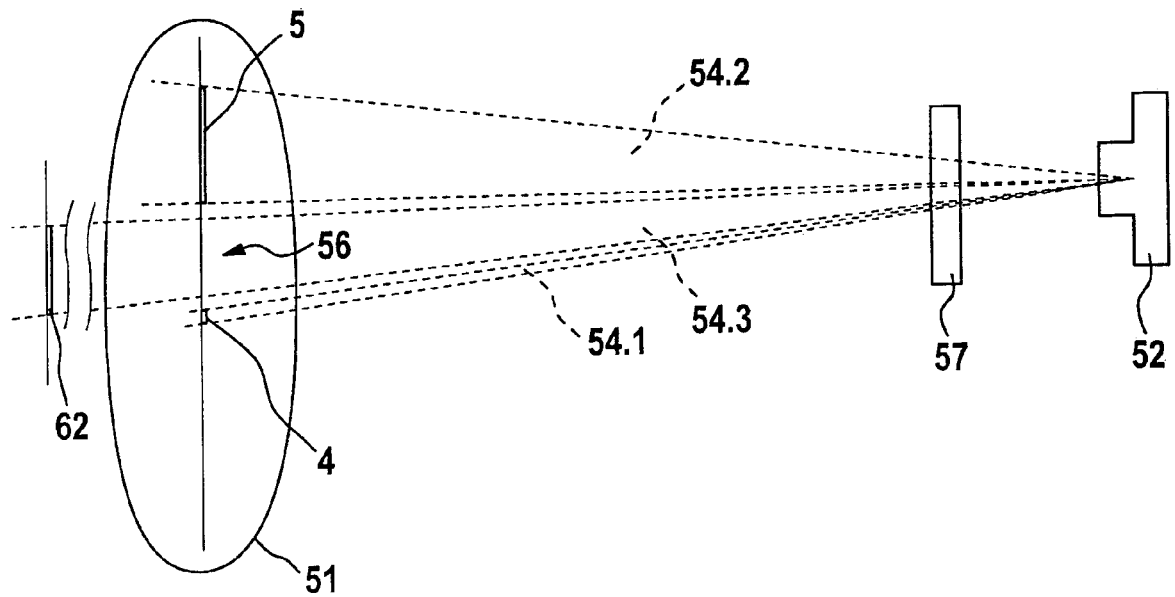
FIG. 5d shows an additional X-ray system having an adjustable primary diaphragm for three imaging positions.

An imaging unit 51 in which there is a radiolucent zone 56 between the two image detectors 4, 5 is illustrated in FIG. 5d. The dimensions of zone 56 are such that a fan beam 54 emitted by X-ray emitter 52 can pass substantially unhindered through the camera.

The camera is stationary in this exemplary embodiment and the fan beam 54.1-54.3 is aimed at the appropriate image detector 4, 5, 62 by an adjustable primary diaphragm 57. To this end, the geometric dimensions of the primary diaphragm 57 are adjusted to the size of the image to be produced. The width for the production of a PAN image is, say, 0.9 mm.

Figure 5E:
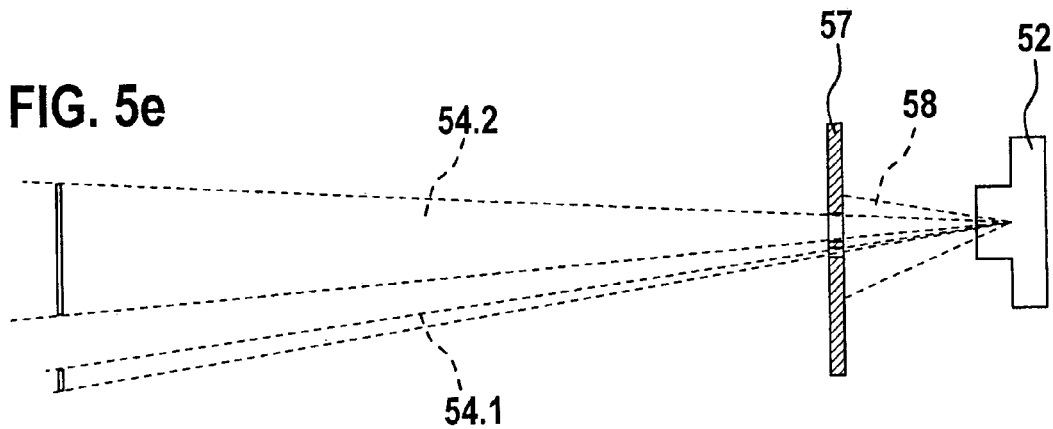
FIGS. 5e and 5f are diagrams illustrating various imaging situations.

This principle is illustrated in detail in FIG. 5e. The primary diaphragm 57 here has two orifices that allow the passage of the appropriate fan beam 54.1, 54.2 for producing the different types of image. The other fan beam is obviously blocked during the production of an image. The cone of radiation 58 produced by the X-ray emitter is sufficiently large to provide the desired fan beam 54.1, 54.2 or, when needed, the fan beam for a teleradiographic image.

Figure 5F:
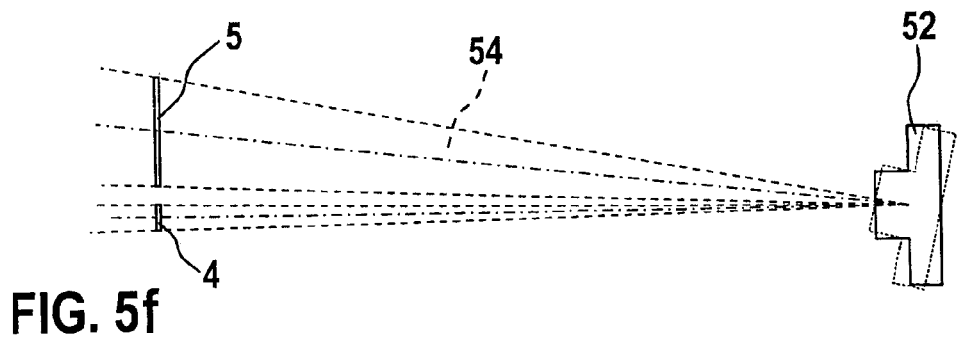

In lieu of splitting the fan beam 58 emitted from the X-ray emitter 52 by an adjustable primary diaphragm, the X-ray emitter 52 can, if desired, be directed, by adjustment mechanisms, toward either one of the image detectors 4, 5, as illustrated in FIG. 5f. Such an adjustment is already known for combined PAN/ceph devices. The adjustment may be achieved by sliding or, as illustrated, by pivoting. The advantage gained in this case is that the central ray of the X-ray fan beam 58 always lies within the fan beam 54.

With the eccentric mounting of the camera 2 illustrated in FIG. 6, a PAN image can be produced in an initial alignment of the camera 2 in which the image detector 4 lies within the X-ray fan beam 54.1. With this alignment of camera 2 it is also possible to produce a ceph image, as the X-ray fan beam 54.3 is directed past camera 2. A multilayer image can be produced when camera 2 is in the position represented by the dashed lines, which is achieved by rotating it about the center of eccentricity 59. In doing so, the image detector 4 is positioned closer to the X-ray fan beam 54.3 for the ceph image than the image detector 5.

The arrangement illustrated has the advantage that a short jib for the ceph camera is sufficient for producing the ceph image, because the X-ray fan beam 54.3 stays close to the wall.

The following fundamental principle must be observed: a different primary diaphragm will be used for the production of a PAN image, a multilayer image, and a ceph image respectively and each image will be created using only one imaging method. When several X-ray fan beams are illustrated together in the exemplary embodiments, this serves merely to clarify the geometric relationships. The primary diaphragm, however, is constructed and adjusted such that the desired image detector is activated by the correct X-ray fan beam for producing the desired image.

The invention claimed is:

1. An X-ray system having a first image detector built into an X-ray-sensitive camera further comprising an X-ray emitter with a primary diaphragm, a second image detector being provided inside said camera, wherein adjustment means are provided for moving, as desired, said first image detector or said second image detector into proper alignment with an X-ray emitter for creation of a respective X-ray image, wherein said adjustment means are provided on a casing of said camera, in connecting means disposed between said camera and a support, or on a support for said camera, wherein the adjustment range of said camera is equal to at least one width of said first image detector, and including an installation for the creation of teleradiographic images with another image detector and, when said X-ray emitter is aligned for the purpose of creating a teleradiographic image, said camera is disposed in the region of the optical path between said X-ray emitter and said image detector of said installation for the creation of teleradiographic images and is radiolucent in said region.

2. An X-ray system having a first image detector built into an X-ray-sensitive camera further comprising an X-ray emitter with a primary diaphragm, a second image detector being provided inside said camera, wherein adjustment means are provided for moving, as desired, said first image detector or said second image detector into proper alignment with an X-ray emitter for creation of a respective X-ray image, wherein said adjustment means are provided on a casing of said camera, in connecting means disposed between said camera and a support, or on a support for said camera, wherein there is additionally provided an installation for the creation of teleradiographic images with another image detector and when said X-ray emitter is aligned for the creation of a teleradiographic image, said camera is movable out of the optical path between said X-ray emitter and said image detector of said installation for the creation of teleradiographic images.

3. An X-ray system as defined in claim 2, wherein said camera is mounted for eccentric adjustment and, in a first position, said image detector for the creation of a first tomographic image is positioned in the path of an X-ray fan beam and, in a second position, said image detector for the creation of a second tomographic image is positioned in the path of the X-ray fan beam.

* * * * *